United States Patent
Chao et al.

(10) Patent No.: US 9,433,773 B2
(45) Date of Patent: Sep. 6, 2016

(54) CRANIAL ELECTROTHERAPY STIMULATION DEVICE

(71) Applicant: Contour Optik Inc., Chiayi (TW)

(72) Inventors: David Chao, Saratoga, CA (US); Chien-Ho Lin, Chiayi (TW); Yung-Chang Chang, Chiayi (TW)

(73) Assignee: Contour Optik Inc., Chiayi (TW)

( * ) Notice: Subject to any disclaimer, the term of this patent is extended or adjusted under 35 U.S.C. 154(b) by 0 days.

(21) Appl. No.: 14/582,554

(22) Filed: Dec. 24, 2014

(65) Prior Publication Data

US 2015/0258327 A1    Sep. 17, 2015

(30) Foreign Application Priority Data

Mar. 14, 2014  (TW) .............................. 103204412 U

(51) Int. Cl.
*A61N 1/00* (2006.01)
*A61N 1/04* (2006.01)
*A61N 1/36* (2006.01)

(52) U.S. Cl.
CPC ........... *A61N 1/0472* (2013.01); *A61N 1/0456* (2013.01); *A61N 1/36025* (2013.01); *A61N 1/0484* (2013.01)

(58) Field of Classification Search
CPC ..... A61N 1/0456; A61N 1/40; A61N 1/0484
See application file for complete search history.

(56) References Cited

U.S. PATENT DOCUMENTS

| | | | |
|---|---|---|---|
| 3,659,614 A * | 5/1972 | Jankelson | A61N 1/321 607/139 |
| 7,437,189 B2 | 10/2008 | Matsumura et al. | |
| 2007/0106143 A1 | 5/2007 | Flaherty | |
| 2010/0204638 A1 | 8/2010 | Hobbs | |
| 2010/0330589 A1 | 12/2010 | Bahrami et al. | |
| 2013/0204315 A1* | 8/2013 | Wongsarnpigoon | A61N 1/36021 607/45 |
| 2014/0142676 A1* | 5/2014 | Gardin | A61N 1/0476 607/139 |
| 2015/0142078 A1* | 5/2015 | Skaribas | A61N 1/0456 607/46 |
| 2015/0217107 A1* | 8/2015 | Walker | A61H 39/002 607/139 |
| 2015/0313496 A1* | 11/2015 | Connor | A61B 5/0476 600/301 |

* cited by examiner

*Primary Examiner* — Robert N Wieland
(74) *Attorney, Agent, or Firm* — Fish & Richardson P.C.

(57) ABSTRACT

A cranial electrotherapy stimulation (CES) device includes a head support, a control unit configured to provide a stimulating current, and a primary arm module. The primary arm module includes a primary arm and an electrode unit. The primary arm is pivotally connected to the head support and is longitudinally extendible. The electrode unit is disposed at the primary arm and includes an electrode that is electrically coupled to the control unit and that forms a path for transmission of the stimulating current to a stimulating point of a subject when the electrode is placed in direct contact with the stimulating point.

27 Claims, 15 Drawing Sheets

CRANIAL ELECTROTHERAPY STIMULATION DEVICE

CROSS-REFERENCE TO RELATED APPLICATION

This application claims priority of Taiwanese Patent Application No. 103204412, filed on Mar. 14, 2014.

FIELD OF THE INVENTION

The invention relates to an electrotherapy stimulation device, more particularly to a cranial electrotherapy stimulation device.

BACKGROUND OF THE INVENTION

In recent years, scientists have discovered that electrotherapy stimulation may be used for treating diseases, alleviating pain, and enhancing blood circulation of a patient. Extensive research in electrotherapy stimulation by several pioneers promotes such treatment to the public and encourages more scientists to participate in electrotherapy stimulation research.

U.S. Patent application Publication No. 20130204315 discloses a conventional system and method of transcranial direct current electrical stimulation (tDCS), which is one kind of cranial electrotherapy stimulation (CES) treatments. However, the structure of the conventional tDCS system is lacking of a relatively flexible structure that is suitable for patients/recipients having various head sizes.

SUMMARY OF THE INVENTION

Therefore, an object of the present invention is to provide a cranial electrotherapy stimulation device that may alleviate the aforementioned drawback associated with the prior art.

One aspect of the present invention is to provide a cranial electrotherapy stimulation device, which includes a head support, a control unit and a primary arm module. The control unit is configured to provide a stimulating current. The primary arm module includes a primary arm and an electrode unit. The primary arm is pivotally connected to the head support and is longitudinally extendible. The electrode unit is disposed at the primary arm, and includes an electrode electrically coupled to the control unit to receive the stimulating current therefrom. The electrode forms a path for transmission of the stimulating current to a stimulating point of a subject when the electrode is placed in direct contact with the stimulating point.

Another aspect of the present invention is to provide a cranial electrotherapy stimulation device which includes a head support, a control unit, a primary arm module and a secondary arm module. The control unit is configured to provide a stimulating current. The primary arm module includes a primary arm that is pivotally connected to the head support. The secondary arm module includes a secondary arm that is rotatably coupled to the primary arm, and an electrode unit that is disposed at the secondary arm and that includes an electrode electrically coupled to the control unit to receive the stimulating current therefrom. The electrode forms a path for transmission of the stimulating current to a stimulating point of a subject when the electrode is placed in direct contact with the stimulating point.

Yet another aspect of the present invention is to provide a cranial electrotherapy stimulation device which includes a clip body, a control unit, an arm member, and an electrode unit. The clip body is configured to be clipped onto a head accessory. The control unit is mounted to the clip body and is configured to provide a stimulating current. The arm member is connected at one end to the clip body. The electrode unit is disposed at the arm member, and includes an electrode electrically coupled to the control unit to receive the stimulating current therefrom. The electrode forms a path for transmission of the stimulating current to a stimulating point of a subject when the electrode is placed in direct contact with the stimulating point.

BRIEF DESCRIPTION OF THE DRAWINGS

Other features and advantages of the present invention will become apparent in the following detailed description of the exemplary embodiments with reference to the accompanying drawings, of which.

DETAILED DESCRIPTION OF THE EXEMPLARY EMBODIMENTS

Figure 1:
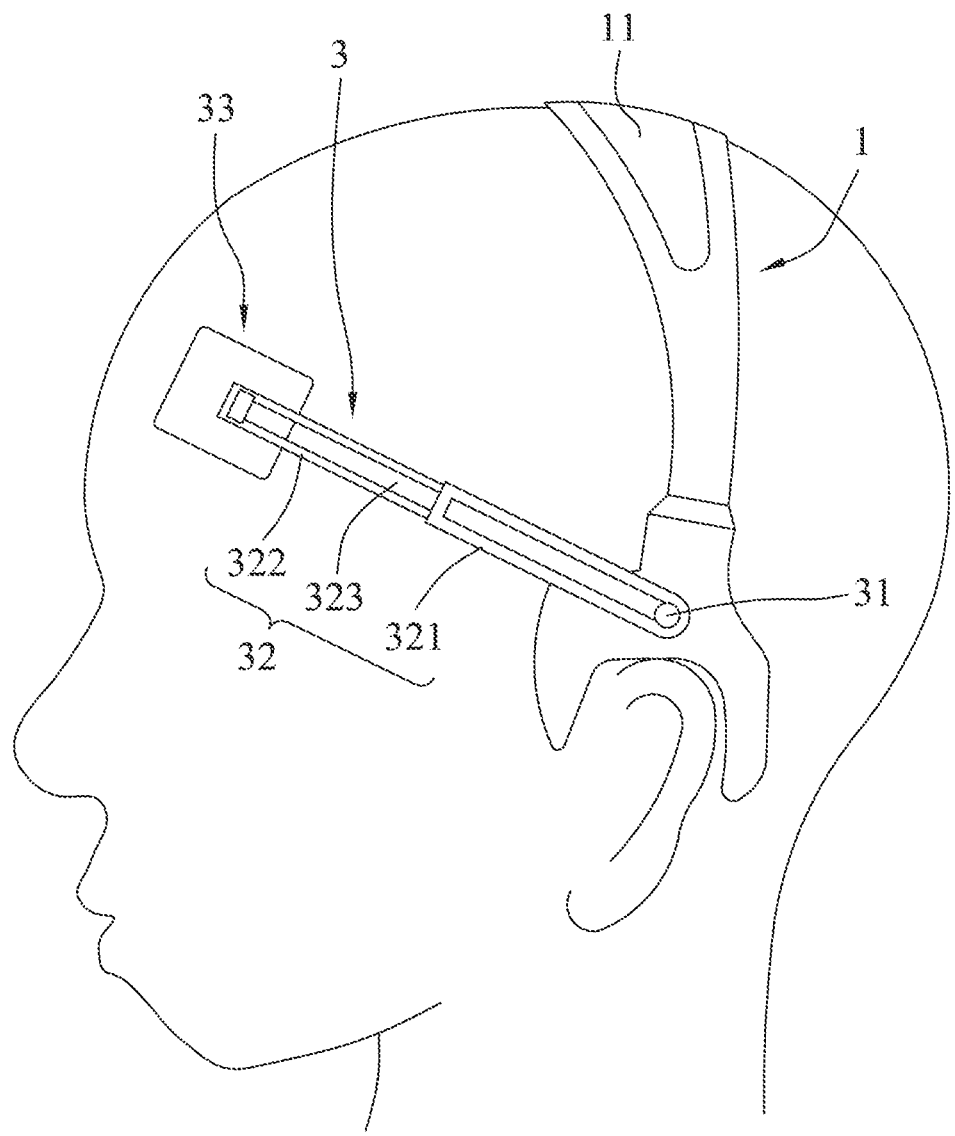
FIG. 1 is a schematic view of a first exemplary embodiment of a cranial electrotherapy stimulation (CES) device according to the invention.

Before the present invention is described in greater detail, it should be noted that like elements are denoted by the same reference numerals throughout the disclosure.

Figure 2:
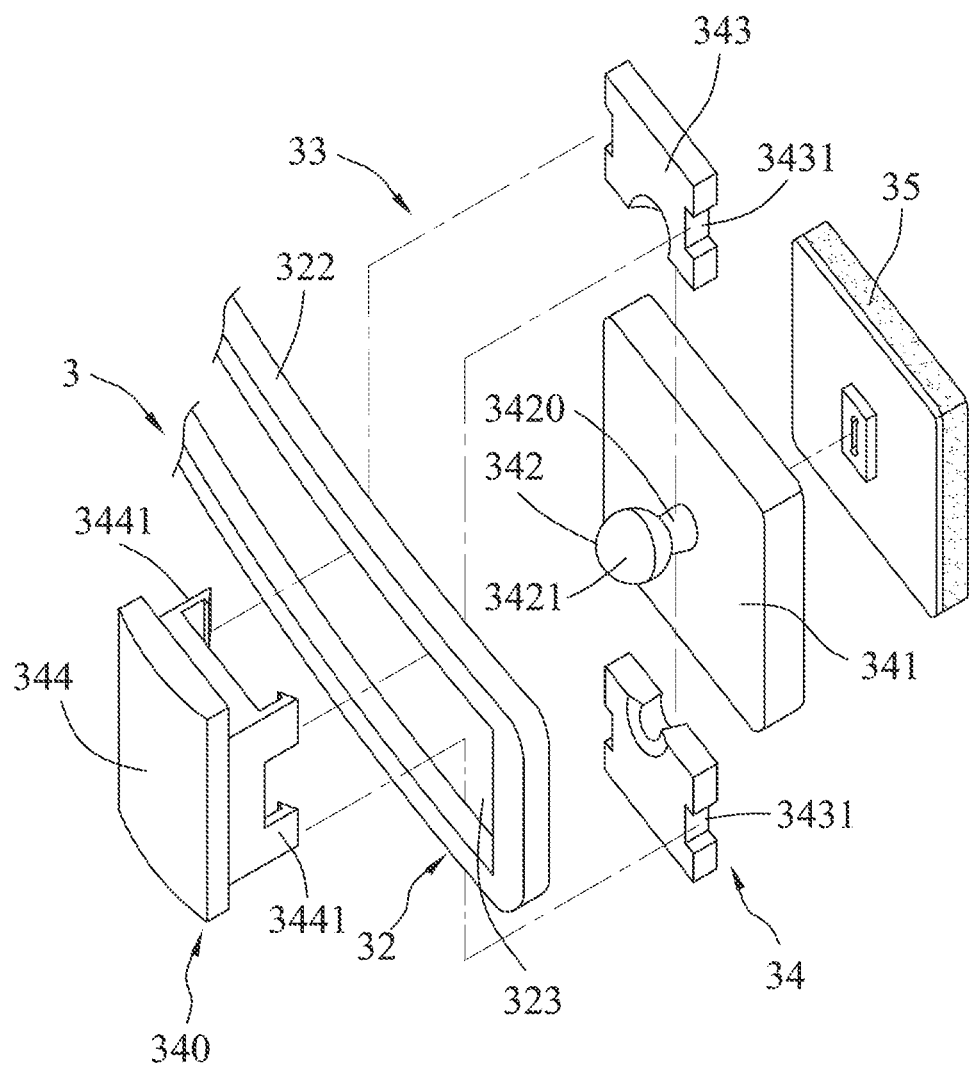
FIG. 2 is a fragmentary exploded perspective view of the first exemplary embodiment, illustrating an electrode unit.
Figure 3:
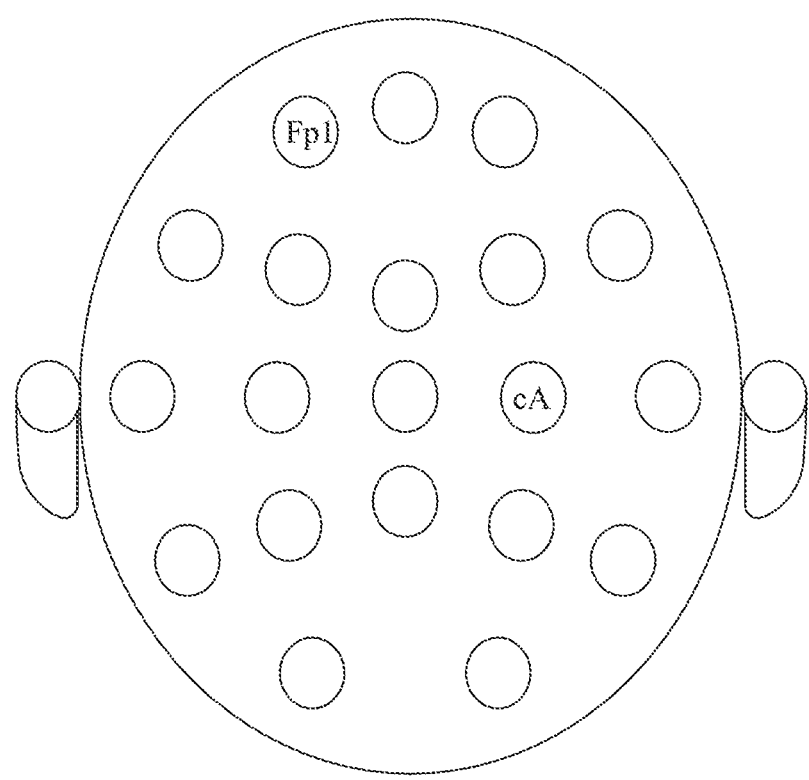
FIG. 3 is a schematic diagram, illustrating multiple stimulating points on a subject's head.

Referring to FIGS. 1 to 3, the first exemplary embodiment of the cranial electrotherapy stimulation (CES) device according to the present invention is shown to include a head support 1, a control unit 11, and a primary arm module 3.

The head support 1 is configured to position the CES device with respect to a subject's head. An exemplary form of the head support 1 is a hair band.

The control unit 11 includes a circuit configured to provide a stimulating current. In this embodiment, the control unit 11 is mounted to the head support 1.

The primary arm module 3 includes a primary arm 32 and an electrode unit 33. The primary arm 32 is pivotally connected to the head support 1 and is longitudinally extendible. In this embodiment, the primary arm 32 is a telescopic arm having a first arm segment 321 pivotally connected to the head support 1, and a second arm segment 322 telescopically coupled to the first arm segment 322.

In this embodiment, as shown in FIG. 1, the primary arm module 3 further includes a pivot joint 31 that pivotally connects the first arm segment 321 of the primary arm 32 to the head support 1 and that releasably retains the primary arm 32 at a desired angular orientation relative to the head support 1. As an example, the pivot joint 31 may include a slot formed in and extending along the first arm segment 321 of the primary arm 32, and a pivot member provided on the head support 1 and coupled slidably and pivotally to the slot.

The electrode unit 33 is disposed at the primary arm 32 and includes an electrode 35 electrically coupled to the control unit 11 to receive the stimulating current therefrom. In this embodiment, the electrode unit 33 is disposed at the second arm segment 322 of the primary arm 32. The electrode 35 forms a path for transmission of the stimulating current to a stimulating point on the subject's head when the electrode 35 is placed in direct contact with the stimulating point. In this embodiment, as shown in FIG. 2, the electrode unit 33 further includes an electrode holder 34 that has the electrode 35 mounted thereon and that is coupled to the second arm segment 322 of the primary arm 32 for sliding movement therealong. In greater detail, the second arm segment 322 of the primary arm 32 is formed with a slot 323 that extends therealong (see FIG. 1), and the electrode holder 34 includes a retaining member 340 that engages slidably the slot 323, and a base member 341 that is connected to the electrode 35 and that is pivotally connected to the retaining member 340 to enable rotation of the electrode 35 relative to the second arm segment 322 of the primary arm 32. To be specific, the retaining member 340 defines a retaining space, and the base member 341 is provided with a ball stud segment 342 which extends away from the electrode 35 and which is retained in the retaining space by the retaining member 340. As shown in FIG. 2, the ball stud segment 342 includes a neck part 3420 connected to the base member 341 and a ball part 3421 connected to the neck part 3420 opposite to the base member 341. The retaining member 340 includes a retaining segment 343 that is disposed adjacent to the base member 341 and that is formed with peripheral engaging grooves 3431, and a cover segment 344 that has peripheral engaging portions 3441 extending through the slot 323 of the second arm segment 322 to engage the peripheral engaging grooves 3431 of the retaining segment 343. The retaining segment 343 and the cover segment 344 cooperate to define the retaining space in this embodiment, the ball part 3421 is confined by the cover segment 344, and the neck part 3420 is engaged by the retaining segment 343 when the ball stud segment 342 is retained in the retaining space.

Figure 6:
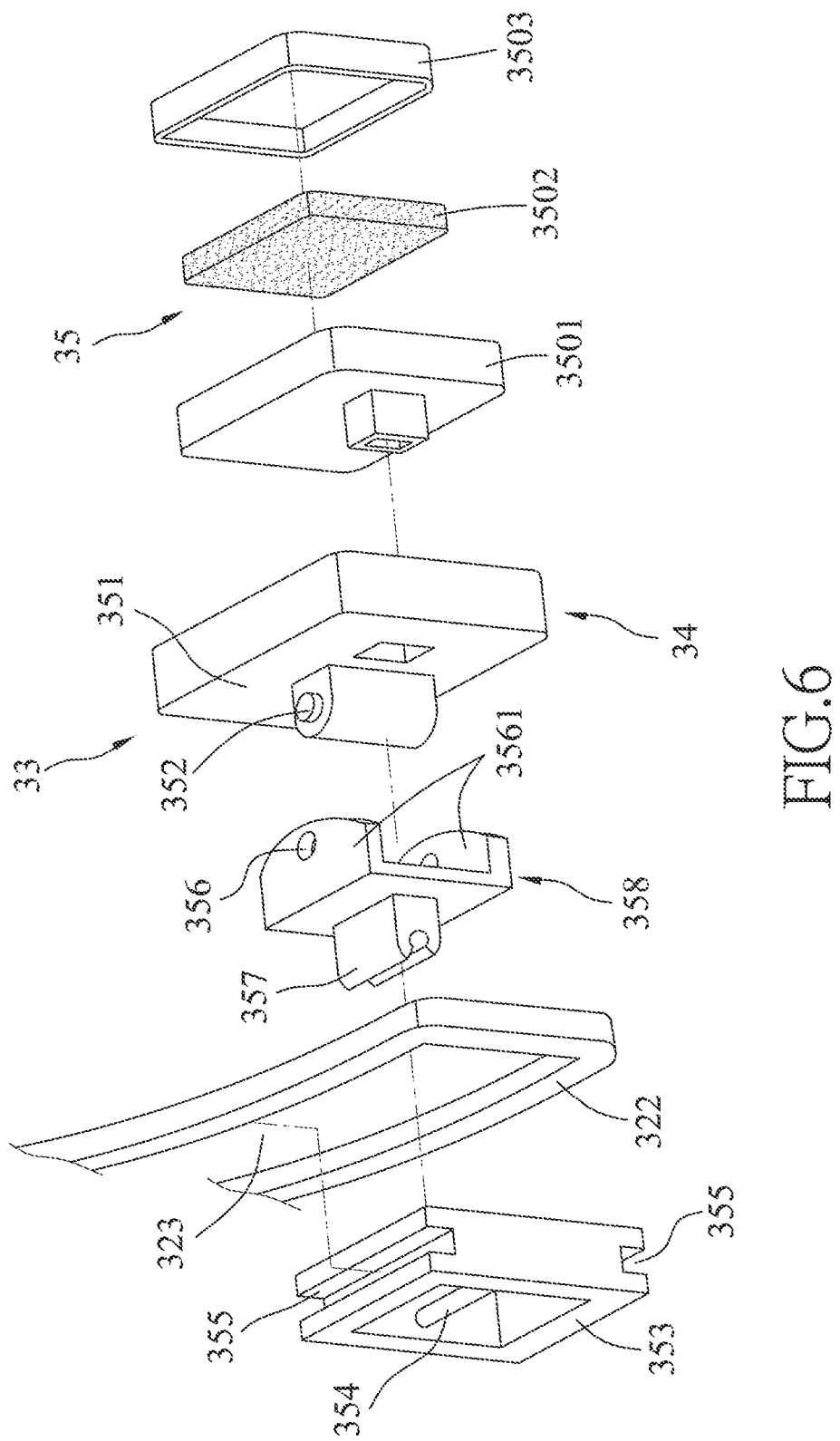
FIG. 6 is a fragmentary exploded perspective view, illustrating a modified electrode unit for use in the first exemplary embodiment.

Further referring to FIG. 6, a variation of the electrode holder 34 of the first exemplary embodiment according to the present invention is illustrated to include a sliding member 353 that is formed with upper and lower engaging grooves 355 to slidably engage upper and lower slot-defining parts that define the slot 323 of the second arm segment 322, a linking member 358 that is coupled to the sliding member 353 and that is rotatable relative to the sliding member 353 about a first axis, and a base member 351 that is connected to the electrode 35 and to the linking member 358 and that is rotatable relative to the linking member 358 about a second axis which is perpendicular to the first axis. In greater detail, one of the sliding member 353 and the linking member 358 has an engaging rod 354 that extends along the first axis, and the other one of the sliding member 353 and the linking member 358 has a first coupling segment 357 that clamps pivotally the engaging rod 354. Moreover, one of the linking member 358 and the base member 351 has a second coupling segment 356 that includes a pair of pivot plates 3561 spaced apart from each other along the second axis, and the other one of the linking member 358 and the base member 351 has an engaging portion 352 that extends along the second axis, that is disposed between the pivot plates 3561, and that has opposite ends pivotally and respectively retained on the pivot plates 3561. In this embodiment, the sliding member 353 has the engaging rod 354, the linking member 358 has the first and second coupling segments 357, 356, and the base member 351 has the engaging portion 352. Such configuration of the electrode holder 34 is easy to assemble/disassemble for the subject/patient.

As shown in FIG. 6, the electrode 35 of the electrode unit 33 includes an electrically-conductive electrode body 3501 that engages the base member 351, and a liquid-retainable contact body 3502 that is electrically and mechanically coupled to the electrode body 3501 and that is configured for transmission of the stimulating current to the stimulating point of the subject when the contact body 3502 is placed in direct contact with the stimulating point. In this embodiment, the electrode 35 further includes a surrounding wall 3503 that cooperates with the base member 351 to define a receiving space to receive the electrode body 3501 and the contact body 3502. It should be noted that, although the shape of the electrode body 3501 is configured to be rectangular in this embodiment, the shape of the electrode body 3501 may be otherwise in other embodiments of the present invention.

FIG. 3 illustrates various stimulating points on the subject's head. When the subject/patient wishes to perform cranium electrotherapy stimulation on one of the stimulating points for attaining a specific function corresponding thereto (e.g., stimulation of the stimulating points cA or FPI may lead to pain alleviation or metabolism improvement), the subject/patient may put the CES device of the present invention onto his/her head and have the electrode 35 positioned at a desired position by rotating the primary arm 32 relative to the head support 1, by adjusting the position of the second arm segment 322 relative to the first arm segment 321, and by sliding the electrode holder 34 along the slot 323 on the second arm segment 322. In addition, the electrode holder 34 is adjustable to further enhance the contact area between the electrode 35 and the stimulating point.

It should be noted that, in some embodiments, the primary arm module 3 may include a plurality of the primary arms 32, and the electrode unit 33 may further include a plurality of the electrodes 35 provided on the primary arms 32.

Figure 4:
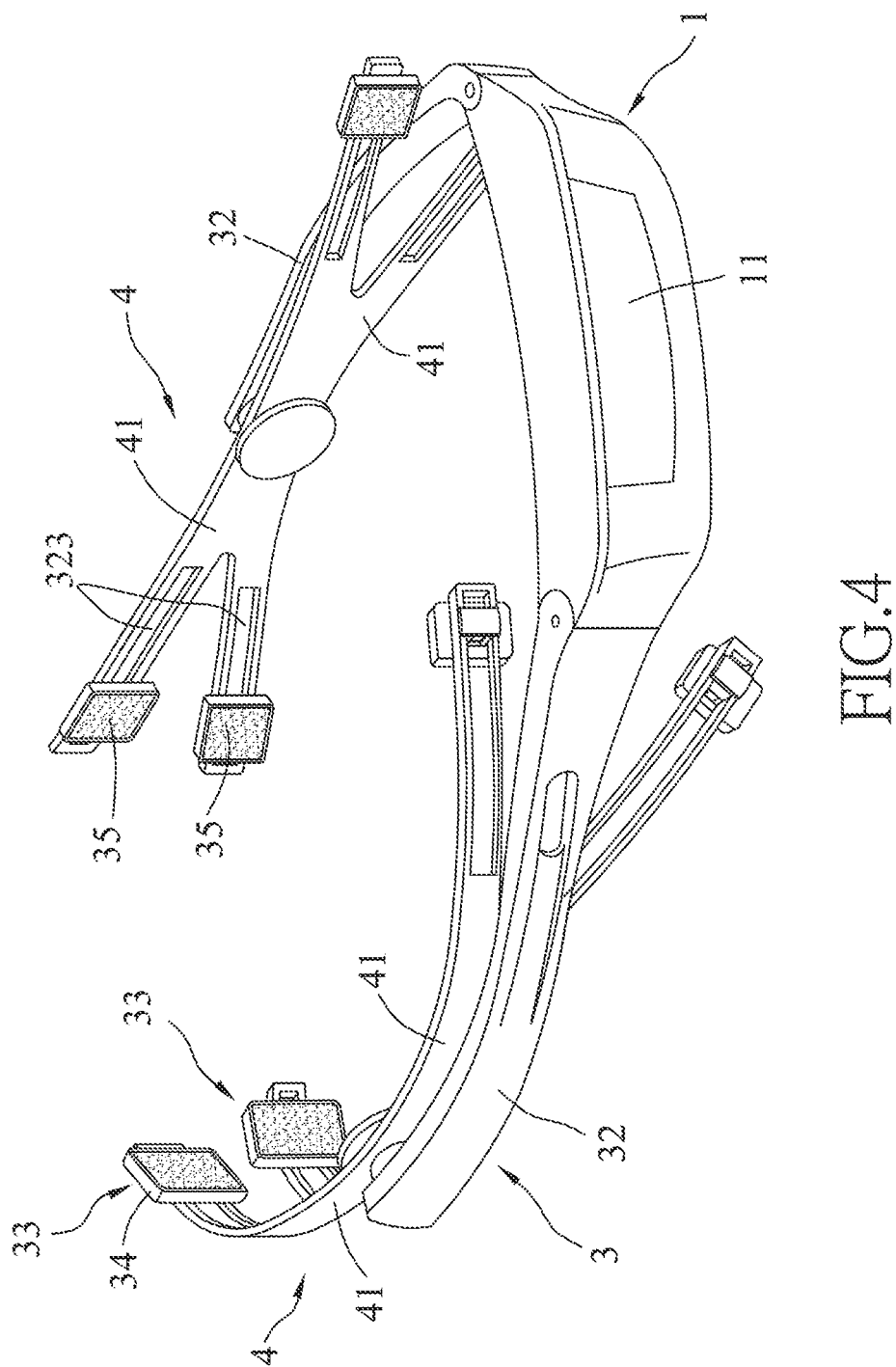
FIG. 4 is a perspective view of a second exemplary embodiment of the CES device according to the present invention.
Figure 5A:
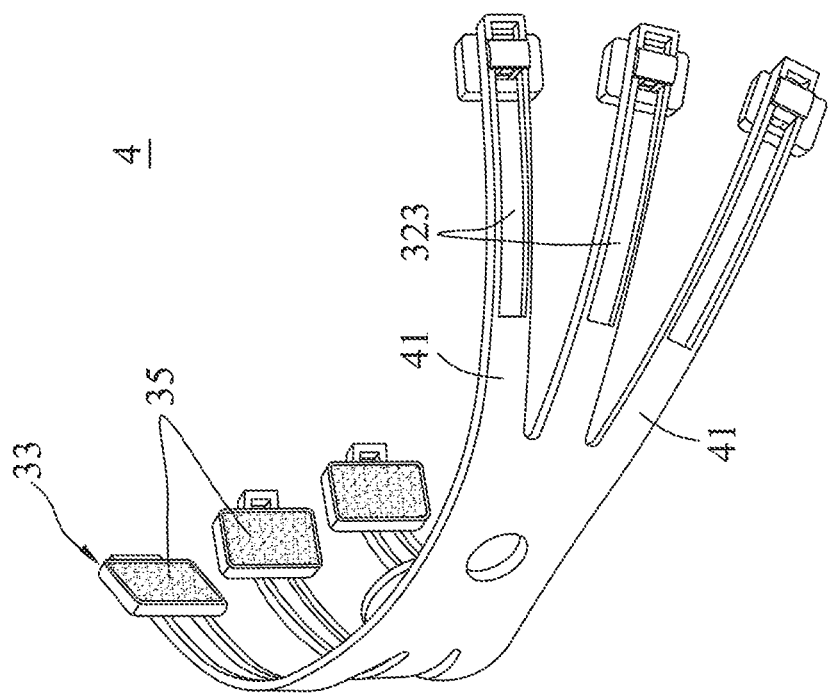
FIG. 5A is a perspective view, illustrating a secondary arm module for use in the second exemplary embodiment.
Figure 5B:
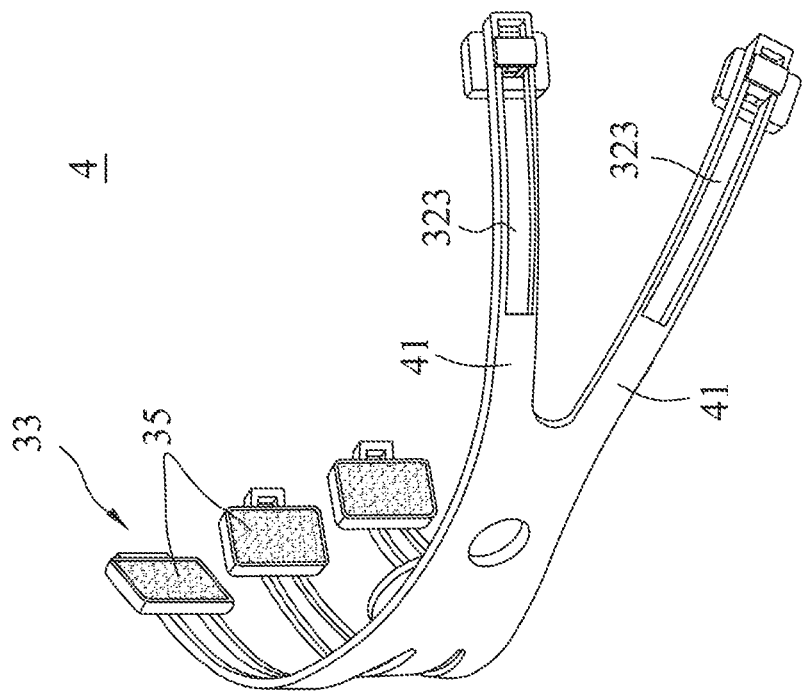
FIG. 5B is a perspective view of another secondary arm module for use in the second exemplary embodiment.

Referring to FIGS. 4, 5A and 5B, the second exemplary embodiment of the cranial electrotherapy stimulation device according to the present invention is shown to be similar to the first exemplary embodiment. The cranial electrotherapy stimulation device of the second exemplary embodiment includes a head support 1, a control unit 11, a primary arm module 3, and a secondary arm module 4. The control unit 11 is configured to provide a stimulating current. The primary arm module 3 includes a primary arm 32 that is pivotally connected to the head support 1. The secondary arm module 4 includes a secondary arm 41 that is rotatably coupled to the primary arm 32, and an electrode unit 33 that is disposed at the secondary arm 41 and that includes an electrode 35 electrically coupled to the control unit 11 to receive the stimulating current therefrom. In this embodiment, the control unit 11 is mounted to the head support 1, and the electrode unit 33 further includes an electrode holder 34 that has the electrode 35 mounted thereon and that is coupled to the secondary arm 41 for sliding movement therealong. In this embodiment, the CES device includes two secondary arm modules 4 each of which includes four secondary arms 41, and the primary arm module 3 includes two primary arms 32 each of which is configured in an arc shape and has opposite ends connected pivotally and respectively to the head support 1 and a respective one of the secondary arm modules 4. Pivotal connection between the primary arm 32 and the head support 1 allows the CES device to be folded into a compact state (not shown). It should be noted that, as shown in FIGS. 5A and 5B, the CES device may include the secondary arm modules 4 having various numbers of the secondary arms 41 for attaining multiple electrotherapy stimulations simultaneously. The configuration of the electrode holder 34 of the second exemplary embodiment may be similar to that of the first exemplary embodiment.

Figure 7:
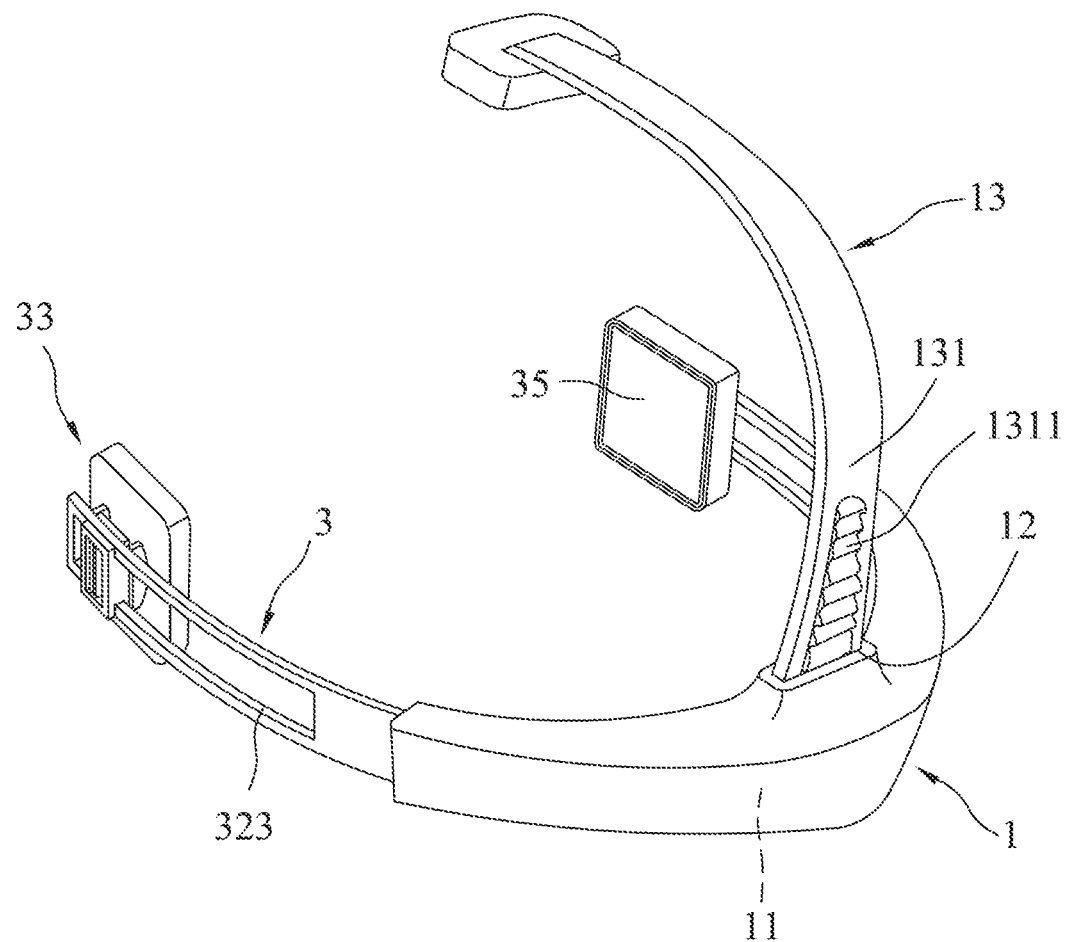
FIG. 7 is a perspective view of a third exemplary embodiment of the CES device according to the present invention.

Referring to FIG. 7, the third exemplary embodiment of the cranial electrotherapy stimulation device according to the present invention is shown to be similar to that of the first exemplary embodiment. The difference between the first and third exemplary embodiments resides in that the cranial electrotherapy stimulation device of the third exemplary embodiment further includes a positioning arm 13 that is adjustably coupled to the head support 1 and that cooperates with the head support 1 to retain removably the CES device on the subject' head. In this embodiment, the head support 1 is formed with a positioning slot 12, and the positioning arm 13 has a positioning portion 131 that is inserted into the positioning slot 12. The positioning portion 131 of the positioning arm 13 is formed with a plurality of positioning projections 1311 to selectively engage the head support 1 at the positioning slot 12, so that a length of the positioning portion 131 that extends out of the positioning slot 12 is variable. Incorporation of the positioning arm 13 into the CES device further enhances retention of the CES device on the subject's head.

Figure 8:
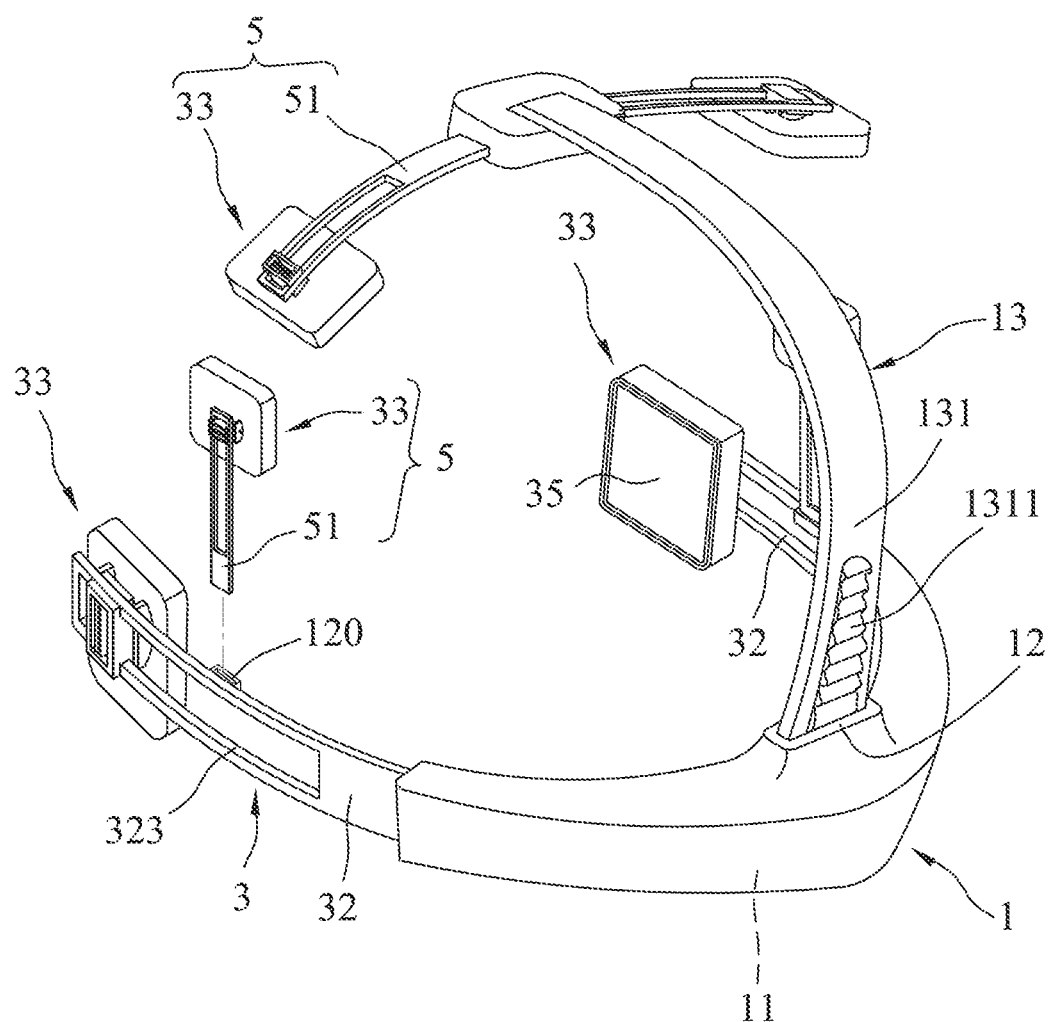
FIG. 8 is a perspective view of a fourth exemplary embodiment of the CES device according to the present invention.

Referring to FIG. 8, the fourth exemplary embodiment of the CES device according to the present invention is shown to be similar to that of the third exemplary embodiment. The difference between the third and fourth exemplary embodiments resides in that the CES device of the fourth exemplary embodiment further includes an auxiliary arm module 5 including an auxiliary arm 51 and an auxiliary electrode unit 33. The auxiliary arm 51 is detachably coupled to one of the positioning arm 13 and the primary arm 32. The auxiliary electrode unit 33 is disposed on the auxiliary arm 51 and includes an auxiliary electrode 35 electrically coupled to the control unit 11 to receive the stimulating current therefrom. The auxiliary electrode 35 forms a path for transmission of the stimulating current to the subject when the auxiliary electrode 35 is placed in direct contact with the subject. In this embodiment, each of the positioning arm 13 and the primary arm 32 is formed with at least one insert slot 120 for insertion of the auxiliary arm 51. Such configuration of the CES device allows the cranial electrotherapy stimulation to be conducted on multiple stimulating points simultaneously.

Figure 9:
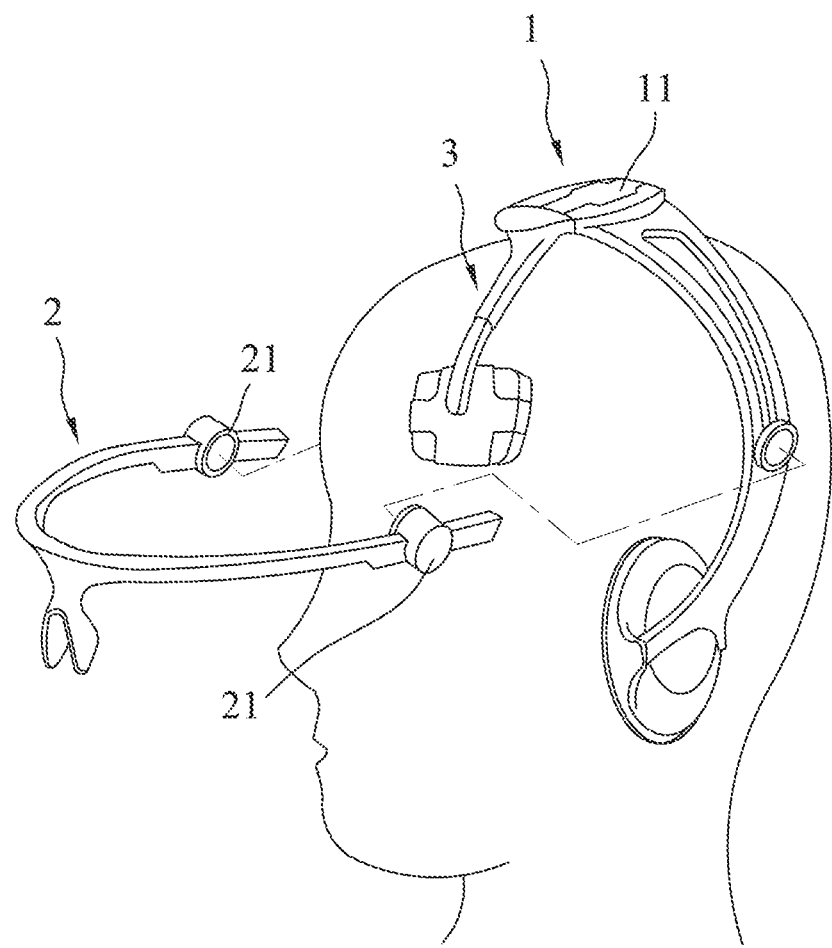
FIG. 9 is a schematic perspective view of a variation of the first exemplary embodiment, illustrating a positioning frame that can be detachably coupled to a head support.

It is worth noting that the CES device of the present invention may further include a positioning frame. As shown in FIG. 9, the CES device of a variation of the first exemplary embodiment includes the positioning frame 2 that is detachably coupled to the head support 1 and that cooperates with the head support 1 to retain removably the CES device on the subject's head. In this embodiment, the positioning frame 2 is arc-shaped, is configured to be positioned on a nose of the subject, and has two opposite ends 21 detachably and pivotally coupled to the head support 1. That is to say, the positioning frame 2 is rotatable to the head support 1 about an axis that passes through the opposite ends 21 thereof. The retention of the CES device can be further ensured by the positioning frame 2.

Figure 10:
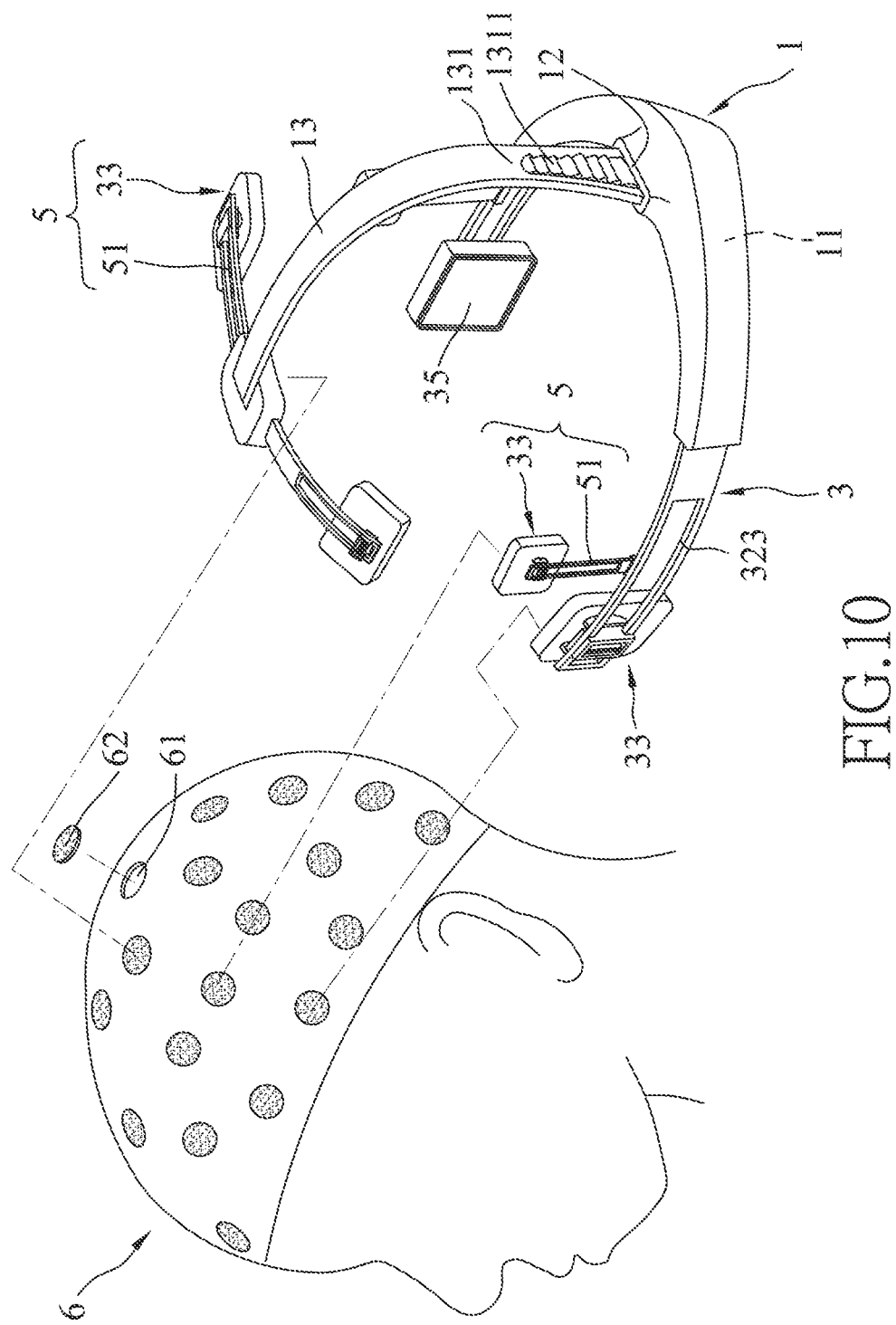
FIG. 10 is a schematic perspective view of a variation of the fourth exemplary embodiment, illustrating that the CES device may further include a cap.

It is also worth noting that the CES device of the present invention may further include a cap. As shown in FIG. 10, which illustrates a variation of the fourth exemplary embodiment, the CES device further includes a cap 6 that is configured to be worn on the subject's head and that is formed with a plurality of positioning holes 61 corresponding in position to the stimulating points of the subject. In greater detail, the cap 6 is made of an elastic material and has a plurality of retaining components 62 which are respectively received in the retaining holes 61 and provide attraction forces for attracting the electrodes 35 onto the cap 6. In this embodiment, the retaining components 62 are magnets and are configured to receive the stimulating current from the electrodes 35 and to transmit the stimulating current to the subject.

Figure 11:
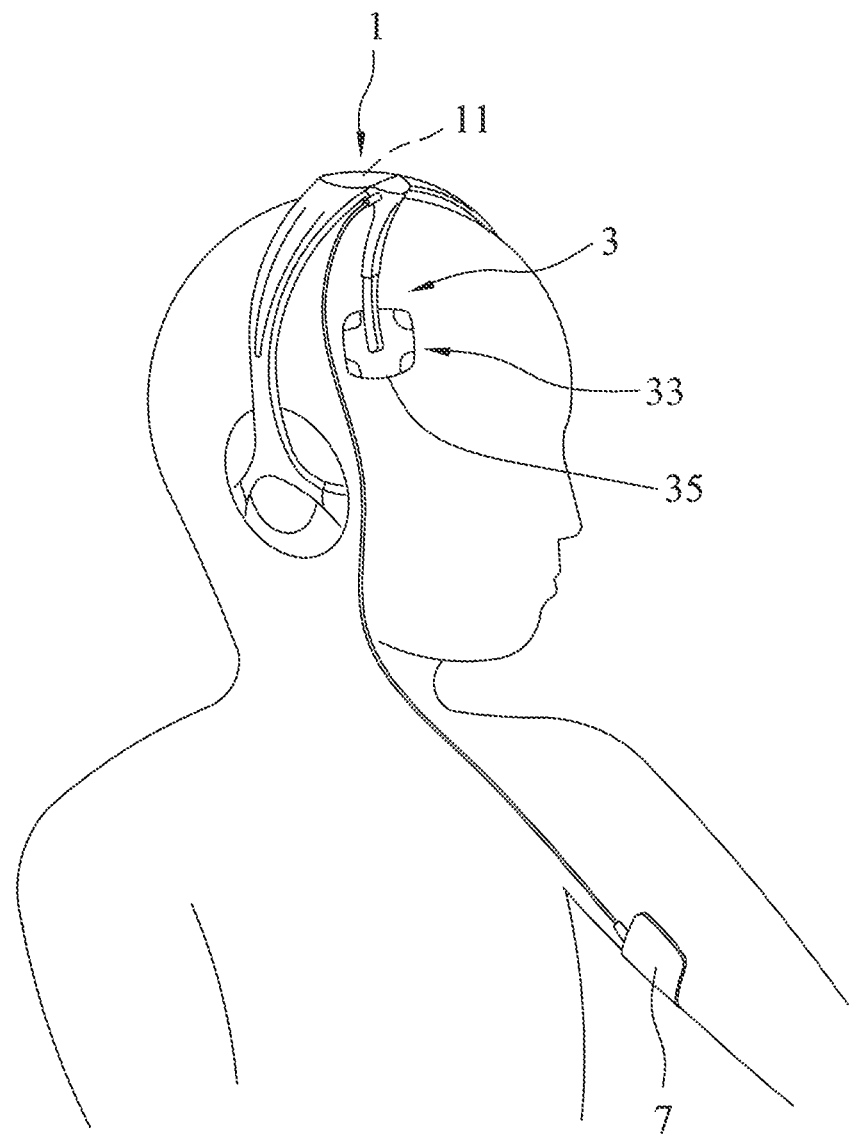
FIG. 11 is a perspective view of another variation of the first exemplary embodiment, illustrating that the CES device may further include a reference electrode.

It is also worth noting that the CES device of the present invention may further include a reference electrode 7. As shown in FIG. 11, which illustrates a variation of the first exemplary embodiment, the CES device includes the reference electrode 7 that is electrically coupled to the control unit 11 and that is configured to be placed in direct contact with a body part the subject for further enhancing the stimulation effect of the CES device.

Figure 12:
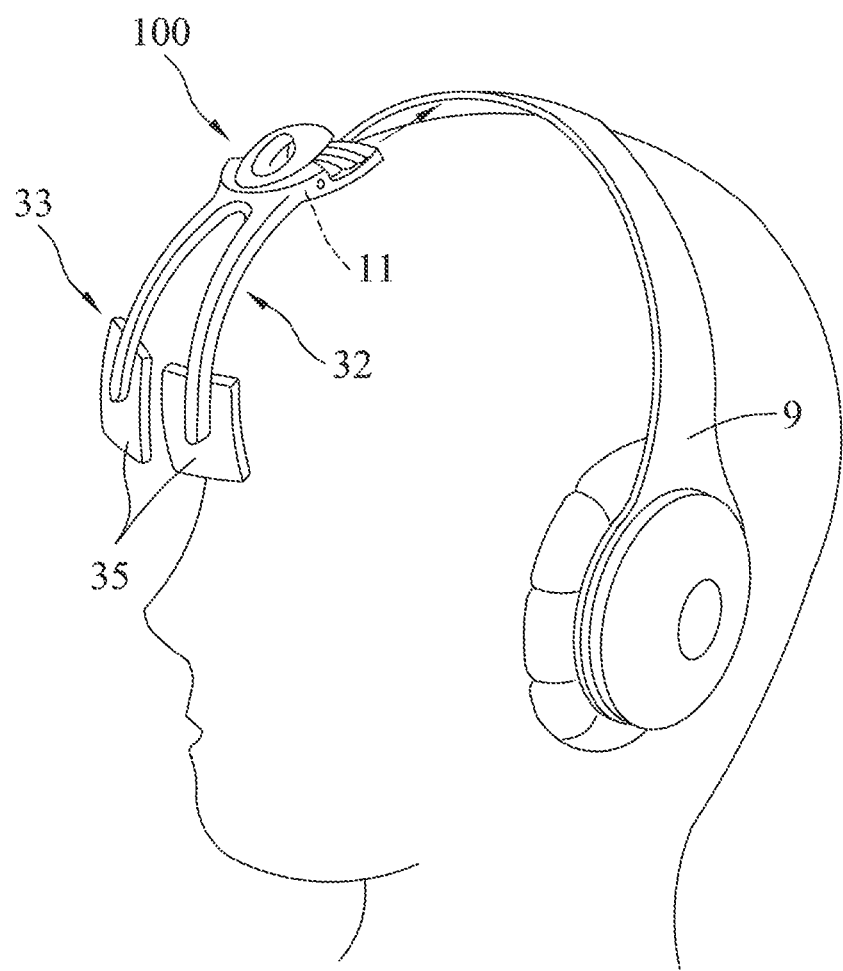
FIG. 12 is a perspective view of a fifth exemplary embodiment of the CES device according to the present invention.

Referring to FIG. 12, the fifth exemplary embodiment of the CES device according to the present invention is shown to include a clip body 100, a control unit 11, an arm member 32, and an electrode unit 33. The clip body 100 is configured to be clipped onto a head accessory 9 (such as a headband or a headphone). The control unit 11 is mounted on the clip body 100 and is configured to provide a stimulating current. The arm member 32 is connected at one end to the clip body 100. The electrode unit 33 is disposed at the arm member 32 and includes an electrode 35 electrically coupled to the control unit 11 to receive the stimulating current therefrom. The electrode 35 forms a path for transmission of the stimulating current to the stimulating point of the subject when the electrode 35 is placed in direct contact with the stimulating point. The arm member 32 may be pivoted to the clip body 100 in other embodiments. The arm member 32 may have a telescopic design in other embodiments. The electrode unit 33 may be slidable along the arm member 32 in other embodiments.

Figure 13:
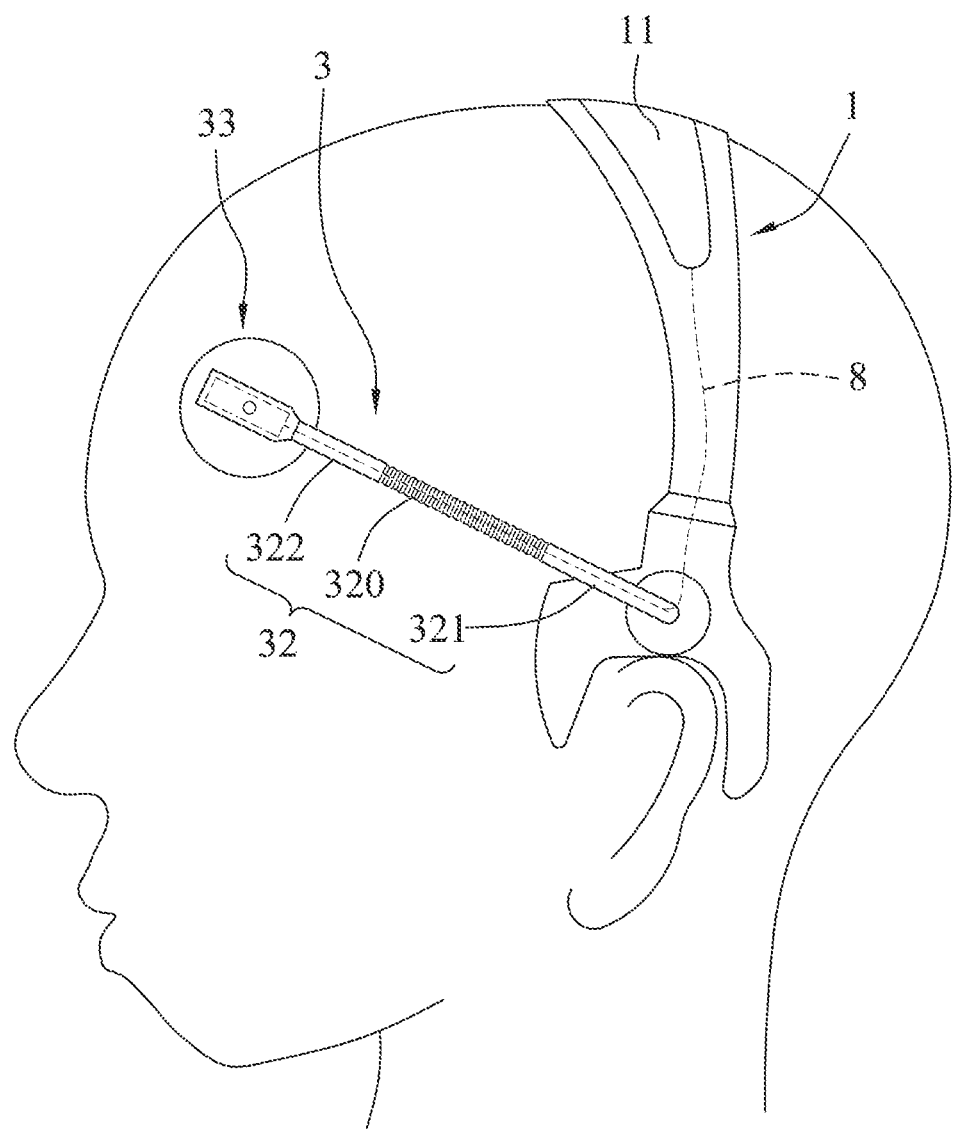
FIG. 13 is a schematic view of a sixth exemplary embodiment of the CES device according to the present invention.
Figure 14:
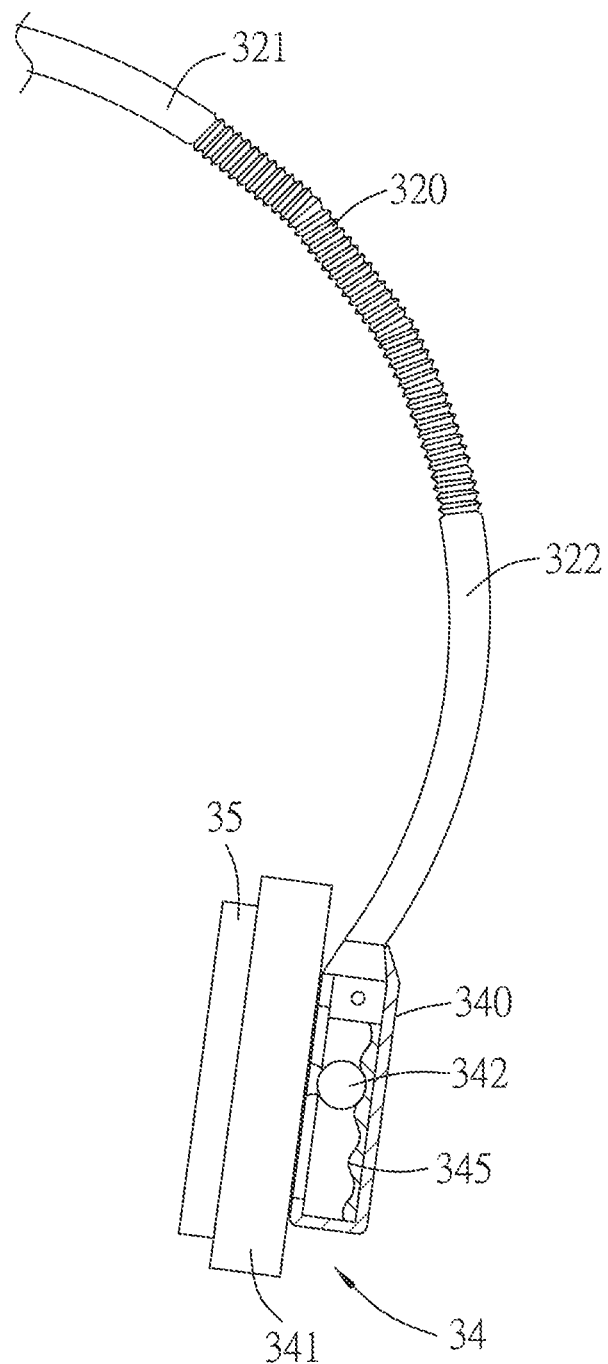
FIG. 14 is a fragmentary partly sectional view, illustrating another modified electrode unit for use in the sixth exemplary embodiment.
Figure 15:
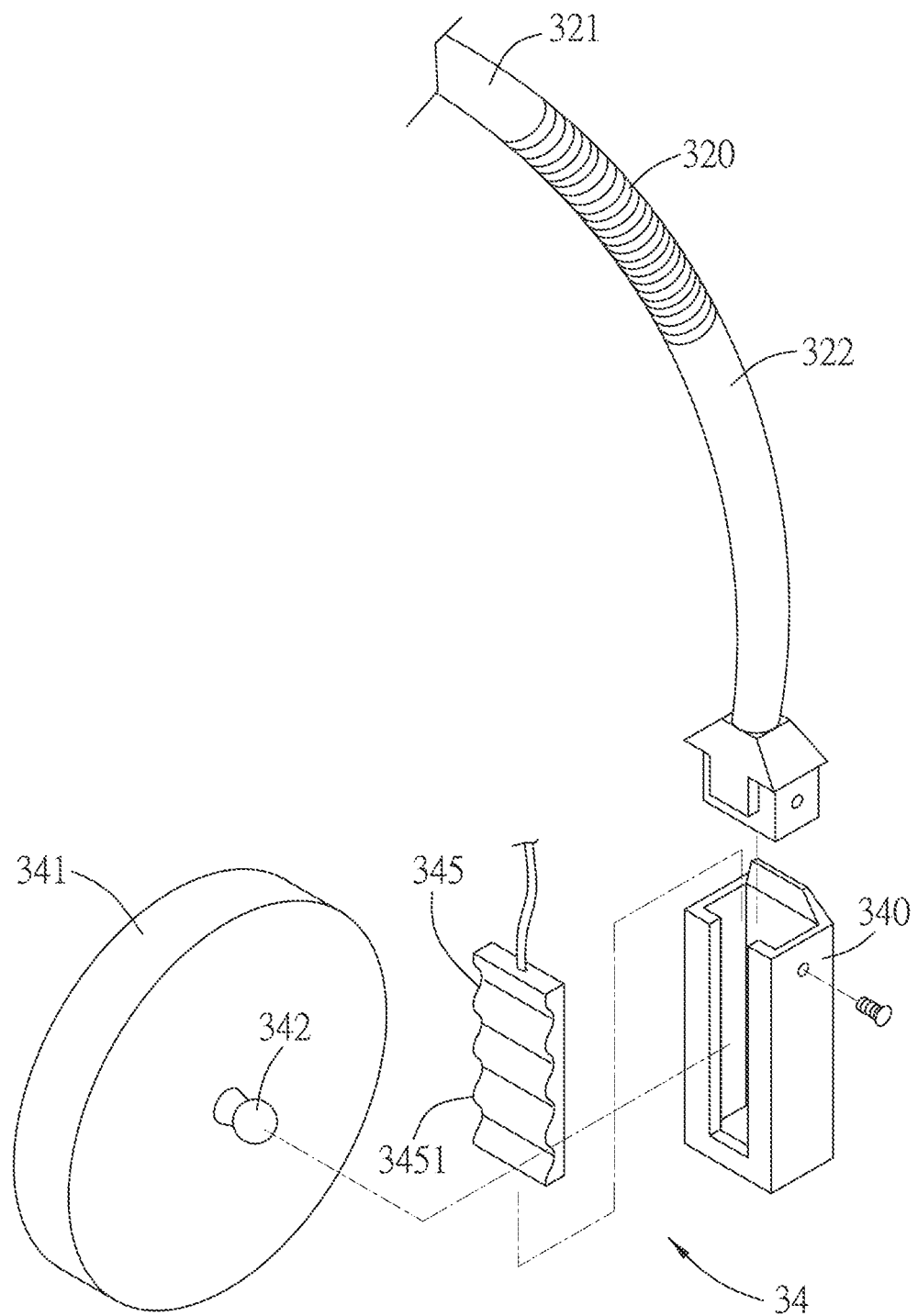
FIG. 15 is a fragmentary exploded perspective view, illustrating the modified electrode unit for use in the sixth exemplary embodiment.

Referring to FIGS. 13 to 15, the sixth exemplary embodiment of the CES device according to the present invention is shown to be similar to that of the first exemplary embodiment. The differences between the first and sixth exemplary embodiments reside in the following.

The primary arm 32 of the primary arm 3 of the sixth exemplary embodiment includes a first arm segment 321 that is pivotally connected to the head support 1, a second arm segment 322 that is provided with the electrode unit 33, and a bellows arm segment 320 that interconnects the first and second arm segments 321, 322 and that is elastically deformable. Moreover, as shown in FIGS. 14 and 15, the electrode holder 34 of the modified electrode unit 33 for use in the sixth exemplary embodiment includes a retaining member 340, a contact member 345, and a base member 341. The retaining member 340 is coupled to the second arm segment 322 of the primary arm 32 and defines a retaining space. The contact member 345 is received in the retaining space, is electrically coupled to the control circuit and is formed with a series of projection portions 3451. In this embodiment, the contact member 345 is configured as a wave-shaped plate having the projection portions 3451 arranged in parallel. The base member 341 is connected to the electrode 35 and is formed with a ball stud segment 342 which is retained in the retaining space and engages selectively an adjacent pair of the projection portions 3451 for transmission of the stimulating current to the electrode 35.

It should be noted that the ball stud segment 342 may slide to engage a different pair of the projection portions 3451 for adjusting the position of the electrode 35 relative to the primary arm 32, and that the ball stud segment 342, which is similar to that of the first embodiment, enables rotation of the electrode 35 relative to the second arm segment 322 of the primary arm 32. It is also worth noting that, in this embodiment, the base member 341 (including the ball stud segment 342) and the contact member 345 may be at least partially made of electrically-conductive material (such as metals) to enable the transmission of the stimulating current by direct contact, and that the contact member 345 may be electrically coupled to the control circuit 11 via electrical wires (see FIG. 13).

While the present invention has been described in connection with what are considered the most practical embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A cranial electrotherapy stimulation (CES) device, comprising:
    a head support;
    a control unit configured to provide a stimulating current; and
    a primary arm module including
        a primary arm that is pivotally connected to said head support, and that is longitudinally extendible, and
        an electrode unit that is disposed at said primary arm and that includes an electrode electrically coupled to said control unit to receive the stimulating current therefrom, said electrode forming a path for transmission of the stimulating current to a stimulating point of a subject when said electrode is placed in direct contact with the stimulating point,
    wherein said primary arm is a telescopic arm having a first arm segment that is pivotally connected to said head support, and a second arm segment that is telescopically coupled to said first arm segment, said electrode unit being disposed at said second arm segment.

2. The CES device according to claim 1, wherein said control unit is mounted to said head support.

3. The CES device according to claim 1, wherein said primary arm module further includes a pivot joint that pivotally connects said first arm segment of said telescopic arm to said head support and that releasably retains said telescopic arm at a desired angular orientation relative to said head support.

4. The CES device according to claim 3, wherein said pivot joint includes a slot formed in and extending along said first arm segment of said telescopic arm, and a pivot member provided on said head support and coupled slidably and pivotally to said slot.

5. The CES device according to claim 1, wherein said electrode unit further includes an electrode holder that has said electrode mounted thereon and that is coupled to said second arm segment of said telescopic arm for sliding movement therealong.

6. The CES device according to claim 5, wherein said second arm segment of said telescopic arm is formed with a slot that extends therealong, and said electrode holder includes
    a retaining member that engages slidably said slot, and
    a base member that is connected to said electrode and that is pivotally connected to said retaining member to enable rotation of said electrode relative to said second arm segment of said telescopic arm.

7. The CES device according to claim 5, wherein said retaining member defines a retaining space, and said base member is provided with a ball stud segment which extends away from said electrode and which is retained in said retaining space by said retaining member.

8. The CES device according to claim 7, wherein:
    said ball stud segment includes a neck part connected to said base member, and a ball part connected to said neck part opposite to said base member;
    said retaining member includes a retaining segment that is disposed adjacent to said base member and that is formed with a peripheral engaging groove, and a cover segment that has a peripheral engaging portion extending through said slot to engage said peripheral engaging groove of said retaining segment;
    said retaining segment and said cover segment cooperating to define said retaining space;
    said ball part being confined by said cover segment and said neck part being engaged by said retaining segment when said ball stud segment is retained in said retaining space.

9. The CES device according to claim 5, wherein said second arm segment of said telescopic arm is formed with a slot therealong, and said electrode holder includes
    a sliding member that slidably engages said slot,
    a linking member that is coupled to said sliding member and that is rotatable relative to said sliding member about a first axis, and
    a base member that is connected to said electrode and to said linking member and that is rotatable relative to said linking member about a second axis which is perpendicular to the first axis.

10. The CES device according to claim 9, wherein:
    one of said sliding member and said linking member has an engaging rod that extends along the first axis; and
    the other one of said sliding member and said linking member has a coupling segment that clamps pivotally said engaging rod.

11. The CES device according to claim 9, wherein:
one of said linking member and said base member has a coupling segment that includes a pair of pivot plates spaced apart from each other along the second axis; and
the other one of said linking member and said base member has an engaging portion that extends along the second axis, that is disposed between said pivot plates, and that has opposite ends pivotally and respectively retained on said pivot plates.

12. The CES device according to claim 9, wherein said electrode includes an electrically-conductive electrode body that engages said base member, and a liquid-retainable contact body that is electrically and mechanically coupled to said electrode body and that is configured for transmission of the stimulating current to the stimulating point of the subject when said contact body is placed in direct contact with the stimulating point.

13. The CES device according to claim 1, further comprising a positioning arm that is adjustably coupled to said head support and that cooperates with said head support to retain removably the CES device on a subject's head.

14. The CES device according to claim 13, wherein said head support is formed with a positioning slot, and said positioning arm has a positioning portion that is inserted into said positioning slot, said positioning portion being formed with a series of positioning projections to selectively engage said head support at said positioning slot so that a length of said positioning portion that extends out of said positioning slot is variable.

15. The CES device according to claim 13, further comprising an auxiliary arm module including:
an auxiliary arm that is detachably coupled to one of said positioning arm and said primary arm; and
an auxiliary electrode unit that is disposed on said auxiliary arm and that includes an auxiliary electrode electrically coupled to said control unit to receive the stimulating current therefrom, said auxiliary electrode forming a path for transmission of the stimulating current to the subject when said auxiliary electrode is placed in direct contact with the subject.

16. The CES device according to claim 15, wherein each of said positioning arm and said primary arm is formed with an insert slot for insertion of said auxiliary arm.

17. The CES device according to claim 1, further comprising a positioning frame that is detachably coupled to said head support and that cooperates with said head support to retain removably the CES device on a subject's head.

18. The CES device according to claim 17, wherein said positioning frame is arc-shaped, is configured to be positioned on a nose of the subject, and has two opposite ends detachably and pivotally coupled to said head support, said positioning frame being rotatable relative to said head support about an axis that passes through said opposite ends thereof.

19. The CES device according to claim 1, further comprising a cap that is configured to be worn on a subject's head and that is formed with a plurality of positioning holes corresponding in position to the stimulating points of the subject.

20. The CES device according to claim 19, wherein said cap has a plurality of retaining components respectively received in said positioning holes, said retaining components providing attraction forces for attracting said electrode onto said cap.

21. The CES device according to claim 1, further comprising a reference electrode that is electrically coupled to said control unit and that is configured to be placed in direct contact with a body part of the subject.

22. A cranial electrotherapy stimulation (CES) device, comprising:
a head support;
a control unit configured to provide a stimulating current and
a primary arm module including
a primary arm that is pivotally connected to said head support, and that is longitudinally extendible, and
an electrode unit that is disposed at said primary arm and that includes an electrode electrically coupled to said control unit to receive the stimulating current therefrom, said electrode forming a path for transmission of the stimulating current to a stimulating point of a subject when said electrode is placed in direct contact with the stimulating point,
wherein said primary arm includes a first arm segment that is pivotally connected to said head support, a second arm segment that is provided with said electrode unit, and a bellows arm segment that interconnects said first arm segment and said second arm segment and that is elastically deformable.

23. The CES device according to claim 22, wherein said electrode unit further includes an electrode holder that has said electrode mounted thereon and that is coupled to said second arm segment of said primary arm.

24. The CES device according to claim 23, wherein said electrode holder includes:
a retaining member that is coupled to said second arm segment of said primary arm and that defines a retaining space;
a contact member that is received in said retaining space, that is electrically coupled to said control circuit and that is formed with a series of electrically-conductive projection portions; and
a base member that is connected to said electrode and that is formed with a ball stud segment which is retained in said retaining space and which engages selectively an adjacent pair of said projection portions for transmission of the stimulating current to said electrode.

25. A cranial electrotherapy stimulation (CES) device, comprising:
a head support;
a control unit that is configured to provide a stimulating current;
a primary arm module including a primary arm that is pivotally connected to said head support; and
a secondary arm module including
a secondary arm that is rotatably coupled to said primary arm, and
an electrode unit that is disposed at said secondary arm and that includes an electrode electrically coupled to said control unit to receive the stimulating current therefrom, said electrode forming a path for transmission of the stimulating current to a stimulating point of a subject when said electrode is placed in direct contact with the stimulating point,
wherein said primary arm has opposite ends connected pivotally and respectively to said head support and said secondary arm.

26. The CES device according to claim 25, wherein said electrode unit further includes an electrode holder that has said electrode mounted thereon and that is coupled to said secondary arm for sliding movement therealong.

27. The CES device according to claim 25, wherein said control unit is mounted to said head support.

* * * * *